United States Patent
Lochmann et al.

(10) Patent No.: US 12,415,774 B2
(45) Date of Patent: *Sep. 16, 2025

(54) POLYOL-BASED ESTERS OF HYDROXYCARBOXYLIC ACIDS

(71) Applicant: KetoLipix Therapeutics GmbH, Hamburg (DE)

(72) Inventors: Dirk Lochmann, Witten (DE); Sebastian Reyer, Witten (DE); Michael Stehr, Witten (DE)

(73) Assignee: KetoLipix Therapeutics GmbH (DE)

( * ) Notice: Subject to any disclaimer, the term of this patent is extended or adjusted under 35 U.S.C. 154(b) by 559 days.

This patent is subject to a terminal disclaimer.

(21) Appl. No.: 17/378,958

(22) PCT Filed: Jan. 23, 2019

(86) PCT No.: PCT/EP2019/051540
§ 371 (c)(1),
(2) Date: Jul. 19, 2021

(87) PCT Pub. No.: WO2020/147979
PCT Pub. Date: Jul. 23, 2020

(65) Prior Publication Data
US 2023/0167046 A1    Jun. 1, 2023

(30) Foreign Application Priority Data

Jan. 17, 2019 (WO) ............. PCT/EP2019/051117

(51) Int. Cl.

| | |
|---|---|
| *C07C 69/675* | (2006.01) |
| *A23L 33/10* | (2016.01) |
| *A61K 31/22* | (2006.01) |
| *A61P 3/02* | (2006.01) |
| *A61P 3/04* | (2006.01) |
| *C07C 67/02* | (2006.01) |
| *C07C 67/03* | (2006.01) |
| *C12P 7/625* | (2022.01) |

(52) U.S. Cl.
CPC ............ *C07C 69/675* (2013.01); *A23L 33/10* (2016.08); *A61K 31/22* (2013.01); *A61P 3/02* (2018.01); *A61P 3/04* (2018.01); *C07C 67/02* (2013.01); *C07C 67/03* (2013.01); *C12P 7/625* (2013.01)

(58) Field of Classification Search
None
See application file for complete search history.

(56) References Cited

U.S. PATENT DOCUMENTS 11,919,851 B2 * 3/2024 Lochmann ............ A23L 33/115
2018/0303821 A1   10/2018 Sonner

FOREIGN PATENT DOCUMENTS

| WO | WO-2004108740 A2 * | 12/2004 | ............ C07C 51/09 |
| WO | WO-2006012490 A2 * | 2/2006 | ............ C07H 13/04 |
| WO | WO-2010021766 A1 * | 2/2010 | ............... A23L 2/52 |
| WO | WO-2013150153 A1 * | 10/2013 | ............. A61K 31/22 |

OTHER PUBLICATIONS

Mierziak ("3-hydroxybutyrate as a metabolite and a signal molecule regulating processes of living organisms" Biomolecules, 2021, p. 402) (Year: 2021).*
Chriett ("Prominent action of butyrate over beta-hydroxybutyrate as histone deacetylase inhibitor, transcriptional modulator and anti-inflammatory molecule", 2019, p. 742) (Year: 2019).*
UCLA (https://web.archive.org/web/20180412232143/https://www.chem.ucla.edu/~harding/IGOC/T/transesterification.html, captured Apr. 12, 2018, downloaded on Jun. 11, 2024) (Year: 2018).*

* cited by examiner

*Primary Examiner* — Amy C Bonaparte
(74) *Attorney, Agent, or Firm* — Edward E. Sowers; Brannon Sowers & Cracraft PC

(57) ABSTRACT

The invention relates to a method for producing polyol esters, especially polyglycerol esters, of 3-hydroxybutyric acid as well as the products thus obtained and their use.

21 Claims, No Drawings

POLYOL-BASED ESTERS OF HYDROXYCARBOXYLIC ACIDS

CROSS-REFERENCES TO RELATED APPLICATIONS

This application is a National Stage filing of International Application PCT/EP 2019/051540 filed Jan. 23, 2019, entitled "METHOD FOR PRODUCING POLYOL-BASED ESTERS OF HYDROXY CABOXYLIC ACIDS", claiming priority to PCT/EP 2019/051117, filed Jan. 17, 2019. The subject application claims priority to PCT/EP 2019/051540 and PCT/EP 2019/051117, and incorporates all by reference herein, in their entirety.

BACKGROUND OF THE INVENTION

The present invention relates to the field of keto bodies and related metabolism and the therapy of related diseases.

Especially, the present invention relates to a method for producing polyol esters of 3-hydroxybutyric acid, especially polyglycerol esters of 3-hydroxybutyric acid, as well as the reaction products thus obtainable or thus prepared (i.e. polyol esters of 3-hydroxybutyric acid, especially polyglycerol esters of 3-hydroxybutyric acid) and their use, especially in pharmaceutical compositions, such as drugs or medicaments, or in food and/or food products, as well as their further applications or uses.

Furthermore, the present invention relates to pharmaceutical compositions, especially drugs or medicaments, comprising the reaction products (i.e. polyol esters of 3-hydroxybutyric acid, especially polyglycerol esters of 3-hydroxybutyric acid) obtainable or produced according to the inventive method, as well as their applications or uses.

Finally, the present invention relates to food and/or food products, especially food supplements, functional foods, novel foods, food additives, food supplements, dietary foods, power snacks, appetite suppressants and strength and/or endurance sports supplements, which comprise the reaction products (i.e. polyol esters of 3-hydroxybutyric acid, especially polyglycerol esters of 3-hydroxybutyric acid) obtainable or produced according to the inventive method, as well as their applications or uses.

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called ketone bodies).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetoacetate) and acetone as well as 3-hydroxybutyric acid (hereinafter also synonymously referred to as beta-hydroxybutyric acid or BHB or 3-BHB) or its salt (i.e. 3-hydroxybutyrate or beta-hydroxybutyrate), the latter being the most important of the three aforementioned compounds. 3-Hydroxybutyric acid or its salt occurs physiologically as the (R)-enantiomer, i.e. as (R)-3-hydroxybutyric acid (synonymously also called (3R)-3-hydroxybutyric acid to emphasize the center of chirality in the 3-position) or its salt.

These keto bodies are also provided physiologically in large amounts from lipids stored in the body by lipolysis during fasting or starvation and replace the energy source glucose almost completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoA-synthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol by the D-beta-hydroxybutyrate dehydrogenase. HMG-CoA is also an end product of the degradation of the amino acid leucine, while acetoacetate is formed during the degradation of the amino acids phenylalanine and tyrosine.

Spontaneous decarboxylation turns acetoacetate into acetone; it can occasionally be perceived in the breath of diabetics and dieters. It cannot be further used by the body. However, the proportion of acetone in the keto bodies is small.

Acetoacetate is thus reductively converted into the physiologically relevant form of 3-hydroxybutyric acid or 3-hydroxybutyrate, but can also decompose into the physiologically unusable acetone with the release of carbon dioxide, which is detectable and olfactory perceptible in severe ketosis, a ketoacidosis (e. g. in diabetes mellitus type 1 patients without insulin substitution), in the urine and in the exhaled air.

3-Hydroxybutyric acid is currently used and marketed in the weight training sector as a sodium, magnesium or calcium salt.

However, 3-hydroxybutyric acid is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect.

In addition, the plasma half-life of 3-hydroxybutyric acid and its salts is so short that even if several grams are taken, the ketosis lasts only for about three to four hours, i.e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i.e. the metabolic conversion of caproic, caprylic and capric acid (i.e. of saturated linear $C_6$-, $C_8$- and $C_{10}$-fatty acids) from the corresponding triglycerides is intended.

Basically, however, from a pharmaceutical and clinical point of view, 3-hydroxybutyric acid is a more effective pharmaceutical-pharmacological target molecule, which, according to the prior art, could in principle be used for the therapy of a large number of diseases, but cannot be used due to its lack of physiological compatibility (e. g. in diseases in connection with a malfunction of the energy metabolism, especially keto-body metabolism, or neurodegenerative diseases such as dementia, Alzheimer's disease, Parkinson's disease, etc., lipometabolic diseases etc.).

The following table illustrates purely exemplary, but by no means limiting, potential therapy options or possible indications for the active ingredient 3-hydroxybutyric acid.

| Indication | Therapeutic effect |
| --- | --- |
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance. BHB offers an immediately effective alternative here. |
| Alzheimer's disease, dementia | Under BHB patients show better cognitive performance. BHB is also effective in the prevention of neurodegenerative diseases. |
| Disorders of fatty acid oxidation (e. g. electron transfer protein defect) | Compensation of a nutrient deficiency in case of defect in energy metabolism, |

Therefore, it is desirable from a pharmaceutical and clinical point of view to be able to find effective precursors or metabolites which physiologically allow direct or indirect access to 3-hydroxybutyric acid or its salts, especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

BRIEF SUMMARY OF THE INVENTION

The problem underlying the present invention is thus the provision of an efficient method for producing physiologically suitable or physiologically compatible precursors and/or metabolites of 3-hydroxybutyric acid (i.e. beta-hydroxybutyric acid or BHB or 3-BHB) or their salts.

Such method should especially make the respective BHB precursors and/or BHB metabolites accessible in an efficient way, especially in larger quantities and without significant amounts of toxic by-products.

In a completely surprising way, the applicant has now discovered that polyol esters, especially polyglycerol esters, of 3-hydroxybutyric acid (beta-hydroxybutyric acid, BHB or 3-BHB) represent an efficient and physiologically effective or physiologically compatible precursor and/or metabolite for the keto body 3-hydroxybutyric acid or its salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing polyol esters, especially polyglycerol esters, of 3-hydroxybutyric acid (beta-hydroxybutyric acid, BHB or 3-BHB) is provided; further, especially special and/or advantageous embodiments of the inventive method are similarly provided.

Furthermore, the present invention relates—according to a second aspect of the present invention—to a reaction product obtainable according to the inventive method or a polyol ester, especially polyglycerol ester, of 3-hydroxybutyric acid (beta-hydroxybutyric acid, BHB or 3-BHB) or a mixture of at least two, especially at least three polyol esters, especially polyglycerol esters, of 3-hydroxybutyric acid (beta-hydroxybutyric acid, BHB or 3-BHB); further, especially special and/or advantageous embodiments of this aspect of the invention are the subject-matter of the relevant claims.

Likewise, the present invention—according to a third aspect of the present invention—relates to a pharmaceutical composition, especially a drug or medicament; further, especially special and/or advantageous embodiments of this aspect of the invention.

Furthermore, the present invention—according to a fourth aspect of the present invention—relates to an inventive reaction product or an inventive polyol ester, especially polyglycerol ester, of 3-hydroxybutyric acid (beta-hydroxybutyric acid, BHB or 3-BHB) or an inventive mixture of at least two, especially at least three polyol esters, especially polyglycerol esters, of 3-hydroxybutyric acid (beta-hydroxybutyric acid, BHB or 3-BHB) for the prophylactic and/or therapeutic treatment or for use in the prophylactic and/or therapeutic treatment of diseases of the human or animal body.

Furthermore, the present invention—according to a fifth aspect of the present invention—relates to the use of an inventive reaction product or an inventive polyol ester, especially polyglycerol ester, of 3-hydroxybutyric acid (beta-hydroxybutyric acid, BHB or 3-BHB) or of an inventive mixture of at least two, especially at least three polyol esters, especially polyglycerol esters, of 3-hydroxybutyric acid (beta-hydroxybutyric acid, BHB or 3-BHB) for the prophylactic and/or therapeutic treatment or for producing a medicament for the prophylactic and/or therapeutic treatment of diseases of the human or animal body.

Furthermore, the present invention—according to a sixth aspect of the present invention—relates to the use of an inventive reaction product or an inventive polyol ester, especially polyglycerol ester, of 3-hydroxybutyric acid (beta-hydroxybutyric acid, BHB or 3-BHB) or an inventive mixture of at least two, especially at least three polyol esters, especially polyglycerol esters, of 3-hydroxybutyric acid (beta-hydroxybutyric acid, BHB or 3-BHB).

Furthermore, the present invention—according to a seventh aspect of the present invention—relates to a food and/or food product; further, especially special and/or advantageous embodiments of the food and/or food product.

Finally, the present invention—according to an eighth aspect of the present invention—relates to the use of an inventive reaction product or an inventive polyol ester, especially polyglycerol ester, of 3-hydroxybutyric acid (beta-hydroxybutyric acid, BHB or 3-BHB) or of an inventive mixture of at least two, especially at least three polyol esters, especially polyglycerol esters, of 3-hydroxybutyric acid (beta-hydroxybutyric acid, BHB or 3-BHB) in a food and/or a food product.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 100% or 100% by weight, respectively, including all components or ingredients, especially as defined below; however, this is self-evident for the person skilled in the art.

In addition, the skilled person may, if necessary, deviate from the following range specifications without leaving the scope of the present invention.

Additionally, it applies that all values or parameters or the like specified in the following can be determined or identified in principle with standardized or explicitly specified determination methods or otherwise with the determination or measurement methods that are otherwise familiar to a person skilled in the art.

Having stated this, the present invention will be described in more detail hereinafter:

DETAILED DESCRIPTION OF THE INVENTION

The subject-matter of the present invention—according to a first aspect of the present invention—is thus a method for producing polyol esters, especially polyglycerol esters, of 3-hydroxybutyric acid (beta-hydroxybutyric acid, BHB or 3-BHB), wherein at least one compound of the general formula (I)

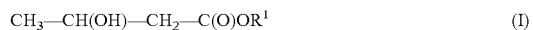
$$CH_3—CH(OH)—CH_2—C(O)OR^1 \quad (I)$$

wherein, in the general formula (I), the radical $R^1$ represents hydrogen or $C_1$-$C_4$-alkyl, especially $C_1$-$C_4$-alkyl, preferably methyl or ethyl, more preferably ethyl, is reacted with at least one polyol (II) comprising at least two hydroxyl groups (OH-groups), especially polyglycerol, so that, as a reaction product, one or more 3-hydroxybutyric acid polyol esters (III), especially 3-hydroxybutyric acid polyglycerol esters, are obtained.

As stated above, the applicant has, quite surprisingly, discovered that the polyol esters, especially polyglycerol esters, of 3-hydroxybutyric acid (beta-hydroxybutyric acid, BHB or 3-BHB)—synonymously also referred to as "3-hydroxybutyric acid polyol ester, especially 3-hydroxybutyric acid polyglycerol ester" (hereinafter briefly referred to as "BHB polyol ester"/"3-BHB polyol ester" or "BHB polyglycerol ester"/"3-BHB polyglycerol ester" or just referred to as "BHB esters"/"3-BHB esters" for short) thus produced are efficient, since physiologically compatible precursors and/or metabolites of 3-hydroxybutyric acid or their salts, which can also be used in larger quantities in pharmaceutical or clinical applications because they are physiologically compatible.

The above-mentioned polyol esters, especially polyglycerol esters, of 3-hydroxybutyric acid, which are accessible for the first time in an efficient manner through the production method according to the invention, represent a physiologically and pharmacologically relevant alternative to free 3-hydroxybutyric acid or its salts.

The production of polyol esters, especially polyglycerol esters, of 3-hydroxybutyric acid by means of conventional organic synthesis is complex and costly, since 3-hydroxybutyric acid has an increased tendency to polymerize and to undergo other undesirable side reactions (e. g. dehydration, decomposition, etc.). Within the scope of the present invention, it was possible for the first time to provide an efficiently working production method with which polyol esters, especially polyglycerol esters, of 3-hydroxybutyric acid can be produced without undesired side reactions, especially in a single step.

The inventive method thus makes it possible for the first time to provide non-toxic polyol esters, especially polyglycerol esters, of 3-hydroxybutyric acid from known, commercially available and above all physiologically harmless components or educts (starting compounds). The resulting polyol esters, especially polyglycerol esters, of 3-hydroxybutyric acid can be broken down physiologically, especially in the stomach and/or bowl, and release or generate the target molecule "3-hydroxybutyric acid" or its salts as active ingredient or active component.

In addition, the aforementioned polyol esters, especially polyglycerol esters, of 3-hydroxybutyric acid also comprise an acceptable taste to ensure compatibility even when administered orally in larger quantities over a longer period of time (e. g. administration of 50 g daily dose or more).

Similarly, the production method according to the invention makes it possible to provide the polyol esters, especially polyglycerol esters, of 3-hydroxybutyric acid free from toxic impurities.

In addition, with appropriate starting materials, the method can also be carried out enantioselectively. For example, according to the invention, the production method allows the biologically relevant form, i.e. the (R)-enantiomer, to be enriched, especially by enzyme catalysis, as not to burden the renal system of patients when administered orally (i.e. elimination via the kidneys). In principle, however, it is also possible, and under certain conditions may be useful, to enrich the (S)-enantiomer.

In addition, the production method according to the invention, including optional further processing or purification steps, can be operated economically and can also be implemented on a large scale.

Especially, the inventive production method uses commercially available starting compounds and furthermore allows a relatively simple process management even in case of large-scale implementation.

In contrast to conventional prior art production methods, the production method according to the invention does not use complex starting materials and uses only a single step.

Nevertheless, excellent yields are achieved in accordance with the invention, wherein the formation of by-products is minimized or avoided.

In addition, the inventive method is simple and economical. Especially, the method according to the invention is usually carried out in the absence of solvents and/or without any solvent (i.e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

The production method according to the invention usually results in a mixture of different polyol esters, especially polyglycerol esters, of 3-hydroxybutyric acid, i.e. in a mixture of at least two, especially at least three polyol esters, especially polyglycerol esters, of 3-hydroxybutyric acid, being different from one another. The resulting raw reaction product or raw mixture can be purified by known methods, especially by removing any remaining starting compounds and/or any by-products present, and furthermore—if desired—can be separated by known methods, especially by distillation and/or chromatography (e. g. fractionation into the individual polyol esters, i.e. mono-, di-, tri- etc. polyol esters of 3-hydroxybutyric acid, or else fractionation into fractions with enriched and depleted portions of individuals etc.).

According to a particular embodiment of the present invention, the compound of the general formula (I) can be used either in racemic form or in the form of the (R)-enantiomer.

The (R)-configuration refers to the chiral carbon atom in the 3-position of the compound of the general formula (I).

According to the invention, it is preferred when, in the general formula (I), the radical $R^1$ represents ethyl.

In other words, according to the invention, it is preferred that, as a compound of the general formula (I), 3-hydroxybutyric acid ethyl ester (ethyl 3-hydroxybutyrate) of the formula $CH_3$—$CH(OH)$—$CH_2$—$C(O)OC_2H_5$ is used.

This enables particularly efficient process control and high yields with minimized or suppressed by-product formation. In addition, the 3-hydroxybutyric acid ethyl ester is also commercially available in large quantities and can also be converted more efficiently than the free acid (i.e. 3-hydroxybutyric acid). Especially, the 3-hydroxybutyric acid ethyl ester can be obtained on a large scale as a starting compound, e. g. by Claisen condensation of ethyl acetate.

Especially, in the inventive method, the reaction is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the present invention, the reaction can be carried out in the presence of a catalyst, especially an enzyme and/or a metal-containing and/or metal-based, acidic or basic catalyst, preferentially in the presence of an enzyme. In this particular embodiment, it is preferred that the catalyst is recycled after the reaction However, as an alternative to this particular embodiment, it is also possible to carry out the reaction autocatalytically or in the absence of a catalyst. However, the use of a catalyst is preferred.

As mentioned above, according to the invention, the reaction can be carried out in the presence of an enzyme as catalyst.

In this context, the enzyme can especially be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

Within the scope of the present invention, the enzyme used as catalyst can especially be derived from *Candida antarctica, Mucor miehei* (*Rhizomucor miehei*), *Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially from *Candida antarctica, Mucor miehei* (*Rhizomucor miehei*) and *Thermomyces lanuginosus*.

According to a specific embodiment, the enzyme can be used in immobilized form, immobilized on a carrier, preferentially on a polymeric carrier, preferably on a polymeric organic carrier, more preferably with hydrophobic properties, even more preferably on a poly(meth)acrylic resin-based carrier.

As explained hereinabove with respect to the use of a catalyst in general, when an enzyme is used as a catalyst, it is preferred to recycle the enzyme after the reaction.

If the reaction is carried out in the presence of an enzyme as a catalyst within the framework of the inventive production method, it is preferred if the reaction is carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

In case of using an enzyme as a catalyst, the amount of the enzyme used can vary within wide range. Especially, the enzyme can be used in amounts, based on the total amount of the starting compounds (I) and (II), in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight. Nevertheless, it may be necessary to deviate from the above-mentioned amounts in individual cases or for specific applications without leaving the scope of the present invention.

If, according to a particular embodiment of the present invention, the reaction is carried out in the presence of an enzyme as a catalyst, the applied pressure range may also vary within a wide range. Especially, if the reaction is carried out in the presence of an enzyme as a catalyst, the reaction can be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the present invention, the reaction can be carried out in the presence of a metal-containing and/or metal-based, acidic or basic catalyst.

According to this alternative embodiment of the present invention, according to which the reaction is carried out in the presence of a metal-containing and/or metal-based, acidic or basic catalyst, the catalyst can especially be selected from (i) basic catalysts, especially alkali or alkaline earth hydroxides and alkali or alkaline earth alcoholates, such as NaOH, KOH, LiOH, Ca(OH)$_2$, NaOMe, KOMe and Na(OBu-tert.), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

According to this embodiment, especially an alkali or alkaline earth alcoholate can be used as a catalyst.

Especially, also according to this embodiment it is preferred if the catalyst based on the metal-containing and/or metal-based, acidic or basic catalyst is recycled after the reaction.

If, according to the particular embodiment of the present invention the reaction is carried out in the presence of a metal-containing and/or metal-based, acidic or basic catalyst, the temperatures can be varied within a wide range. Especially, the reaction can be carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, also according to this embodiment, the catalyst (i.e. the metal-containing and/or metal-based, acidic or basic catalyst) can also be varied within wide quantity ranges: For example, the catalyst based on a metal-containing and/or metal-based, acidic or basic catalyst can be used in amounts, based on the total amount of the starting compounds (I) and (II), in the range of from 0.01 to 30% by weight, especially in the range of from 0.05 to 15% by weight, preferentially in the range of from 0.1 to 15% by weight, preferably in the range of from 0.2 to 10% by weight. Nevertheless, it is possible to deviate from the above-mentioned amounts for specific applications or individual cases without leaving the scope of the present invention.

If, according to this particular embodiment of the present invention, the reaction is carried out in the presence of a metal-containing and/or metal-based, acidic or basic catalyst, the pressure range can equally vary within a wide range: Especially, the reaction can be carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

As far as the quantity of starting materials or starting compounds is concerned, this can also be varied within a wide range.

Taking into account process economy and optimization of the course of the method, especially with regard to the minimization of by-products, it is advantageous if the compound of the general formula (I), based on the hydroxyl groups of the polyol (II), especially polyglycerol, is used in molar amounts in a range of from equimolar amount up to a molar excess of 200 mol-%, especially in a range of from equimolar amount up to a molar excess of 150 mol-%, preferentially in a range of from equimolar amount up to a molar excess of 100 mol-%.

Similarly, taking into account process economy and optimization of the course of the method, especially with regard to minimizing by-products, it is advantageous if the compound of the general formula (I) and the polyol (II), especially polyglycerol are used in a molar ratio of compound of the general formula (I)/polyol (II) in a range of from 1:1 to 10:1, especially in a range of from 2:1 to 8:1, preferably in a range of from 3:1 to 6:1.

As far as the polyol (II) usable in the method according to the invention is concerned, it is particularly preferred if the polyol (II) comprises at least three hydroxyl groups (OH-groups)).

According to a special embodiment of the inventive method, it may especially be provided that the polyol (II) corresponds to the general formula (IIa)

(HO)$_m$—(X)—(OH)$_n$  (IIa)

wherein, in the general formula (IIa),

X represents an organic radical, especially a preferentially saturated organic radical comprising 4 to 20 carbon atoms and optionally comprising 1 to 9 oxygen atoms, preferentially selected from an alkyl radical or a (poly)alkyl ether radical, especially (poly)alkylene glycol radical, more preferably selected from a C$_4$-C$_{20}$-alkyl radical or a C$_4$-C$_{20}$-(poly)alkyl ether radical, especially a C$_4$-C$_{20}$-(poly)alkylene glycol radical; and the variables m and n, each independently of one another, represent an integer from 1 to 10.

Especially, according to the invention, it is preferred in this context that the hydroxyl groups of the polyol (II) are in any position of the radical X, preferentially wherein at least one hydroxyl group is terminal (i.e. being a primary hydroxyl group). This means in particular that the hydroxyl groups can be located or provided in any position of the organic radical X (preferably, however, with the proviso that at least one hydroxyl group is terminal and/or is a primary hydroxyl group).

Especially, the polyol (II), which can be used within the scope of the inventive method, may be selected from polyether polyols and alkane polyols and combinations thereof, especially C$_4$-C$_{20}$-polyether polyols and C$_4$-C$_{20}$-alkane polyols, preferentially C$_4$-C$_{20}$-polyether polyols and C$_4$-C$_{20}$-alkane diols, more preferably polyether polyols, even more preferably C$_4$-C$_{20}$-polyether polyols According to a particular embodiment of the method according to the invention, the polyol (II) may be selected from polyether polyols, especially C$_4$-C$_{20}$-polyether polyols, preferentially polyglycerols of the general formula (IIb)

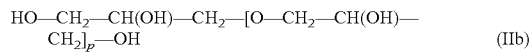

HO—CH$_2$—CH(OH)—CH$_2$—[O—CH$_2$—CH(OH)—CH$_2$]$_p$—OH  (IIb)

wherein, in the general formula (IIb), the variable p represents an integer from 1 to 4, especially 1 or 2, preferentially 1.

According to another special embodiment of the method according to the invention, the polyol (II) may be a diglycerol of formula (IIc)

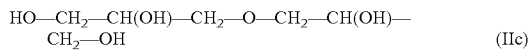
(IIc)

According to a further special embodiment of the method according to the invention, the polyol (II) may be selected from alkanediols, especially $C_4$-$C_{20}$-alkanediols, preferentially linear or branched alkanediols, preferably linear or branched $C_4$-$C_{20}$-alkanediols, more preferably linear $C_4$-$C_{20}$-alkanediols, even more preferably linear $C_4$-$C_{20}$-alkanediols having at least one terminal and/or primary hydroxyl group, yet even more preferably pentanediol, especially 1,2-pentanediol.

According to a preferred embodiment of the present invention, the present invention according to this aspect of the invention relates to a method for producing polyol esters, especially polyglycerol esters, of 3-hydroxybutyric acid (beta-hydroxybutyric acid, BHB or 3-BHB), especially a method as defined hereinabove, wherein at least one compound of the general formula (I)

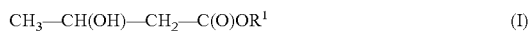
(I)

wherein, in the general formula (I), the radical $R^1$ represents hydrogen or $C_1$-$C_4$-alkyl, especially $C_1$-$C_4$-alkyl, preferably methyl or ethyl, more preferably ethyl, is reacted with at least one polyol (II) comprising at least two hydroxyl groups (OH-groups), especially polyglycerol, wherein the polyol (II) is selected from polyether polyols, especially $C_4$-$C_{20}$-polyether polyols, preferentially polyglycerols of the general formula (IIb)

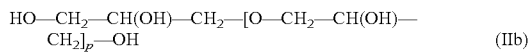
(IIb)

wherein, in the general formula (IIb), the variable p represents an integer from 1 to 4, especially 1 or 2, preferentially 1, so that, as a reaction product, one or more 3-hydroxybutyric acid polyol esters (III), especially 3-hydroxybutyric acid polyglycerol esters, are obtained.

According to another preferred embodiment of the present invention, the present invention according to this aspect of the invention relates to a method for producing polyol esters, especially polyglycerol esters, of 3-hydroxybutyric acid (beta-hydroxybutyric acid, BHB or 3-BHB), especially a method as defined hereinabove, wherein at least one compound of the general formula (I)

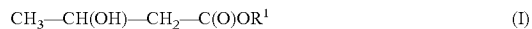
(I)

wherein, in the general formula (I), the radical $R^1$ represents ethyl, is reacted with at least one polyol (II) comprising at least two hydroxyl groups (OH-groups), especially polyglycerol, wherein the polyol (II) is selected from polyglycerols of the general formula (IIb)

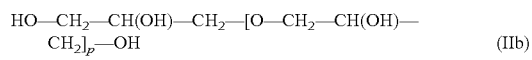
(IIb)

wherein, in the general formula (IIb), the variable p represents an integer 1 or 2, preferentially 1, so that, as a reaction product, one or more 3-hydroxybutyric acid polyol esters (III), especially 3-hydroxybutyric acid polyglycerol esters, are obtained.

The following reaction or synthesis scheme illustrates an approach which is particularly preferred according to the invention (wherein depending on the reaction control, either individual esters or a mixture of two or more of them are obtained):

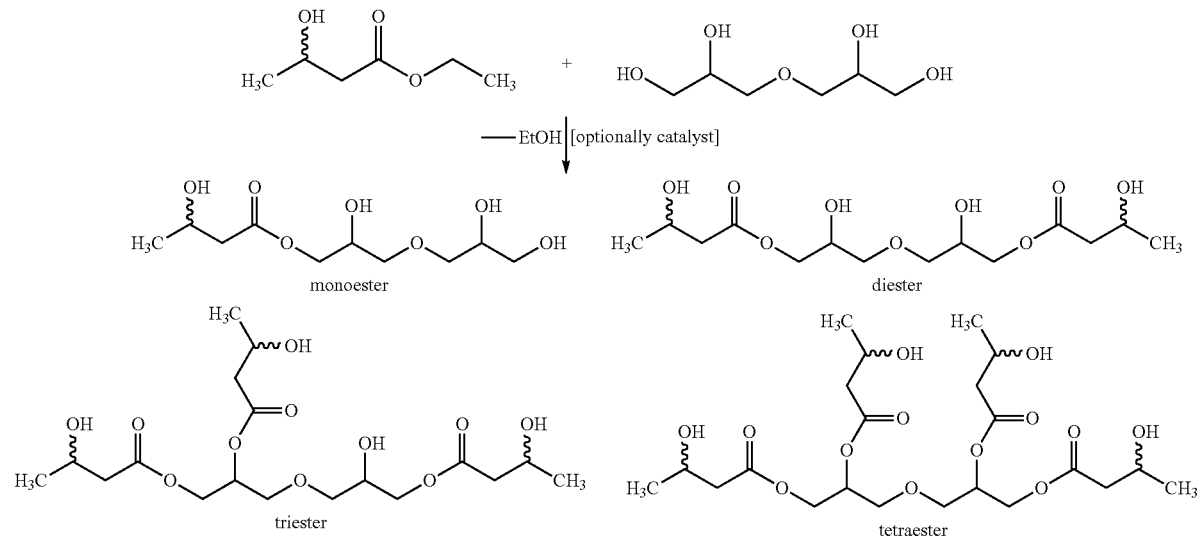

In the method according to the invention, during the reaction, the compound according to the general formula (IV)

(IV)

is formed simultaneously, wherein, in the general formula (IV), the radical $R^1$ represents hydrogen or $C_1$-$C_4$-alkyl, especially $C_1$-$C_4$-alkyl, preferably methyl or ethyl, more preferably ethyl.

Especially, it is preferred in this context if the compound according to the general formula (IV) is withdrawn from the reaction, especially continuously withdrawn, especially by means of preferentially continuous removal by distillation. In this way, the reaction equilibrium is efficiently shifted to the side of the reaction products. Also, the formation of by-products is minimized or prevented in this way.

Within the scope of the inventive production method, the reaction product, especially the composition of the reaction product, especially the presence of the various 3-hydroxybutyric acid polyol esters (III), especially 3-hydroxybutyric acid polyglycerol esters, and their proportion in the case of a mixture, may be controlled and/or regulated by means of the reaction conditions, especially by selecting the reaction temperature (conversion temperature) and/or by selecting the reaction pressure (conversion pressure) and/or by providing a catalyst and selecting such catalyst with respect to the type and/or amount and/or by selecting the amounts of starting compounds (educts) and/or by providing the removal of the compound according to the general formula (IV) as defined above.

After the reaction, the reaction product obtained can be subjected to further purification or work-up steps.

In this context, the reaction product obtained can be fractionated after the reaction has been performed, especially fractionated by distillation.

Also, unreacted starting compounds (I) and/or (II) can be separated from the reaction product and subsequently recycled.

According to a special embodiment of the production method according to the invention, it is especially possible to proceed in such a way that hydroxyl groups still present in the reaction product after the reaction has been performed are at least partially, preferentially completely, functionalized, especially esterified. Especially, the reaction can be followed by a partial, especially complete functionalization, especially esterification, of hydroxyl groups still present.

In this particular embodiment of the inventive method, especially the functionalization, especially esterification, of the hydroxyl groups can be carried out by reaction with a carboxylic acid anhydride, especially $C_2$-$C_{30}$-carboxylic acid anhydride, preferably $C_2$-$C_{10}$-carboxylic acid anhydride, preferentially $C_7$-carboxylic acid anhydride. The $C_2$-$C_{30}$-carboxylic acid anhydride, preferably $C_2$-$C_{10}$-carboxylic acid anhydride, preferentially $C_7$-carboxylic acid anhydride, can be a linear (straight-chain) or branched, saturated or mono- or polyunsaturated $C_2$-$C_{30}$-carboxylic acid anhydride, preferably $C_2$-$C_{10}$-carboxylic acid anhydride, preferentially $C_7$-carboxylic acid anhydride.

A particularly preferred approach according to the invention, which includes a functionalization, especially esterification, of hydroxyl groups still present following the reaction, is illustrated by the following reaction or synthesis scheme (wherein, depending on the reaction control during the reaction, either individual esters or a respective mixture of two or more thereof are obtained and wherein, in the following reaction or synthesis scheme, the radical R represents a radical of the formula $CH_3$—$(CH_2)_{x=0-28}$—$C(O)$—):

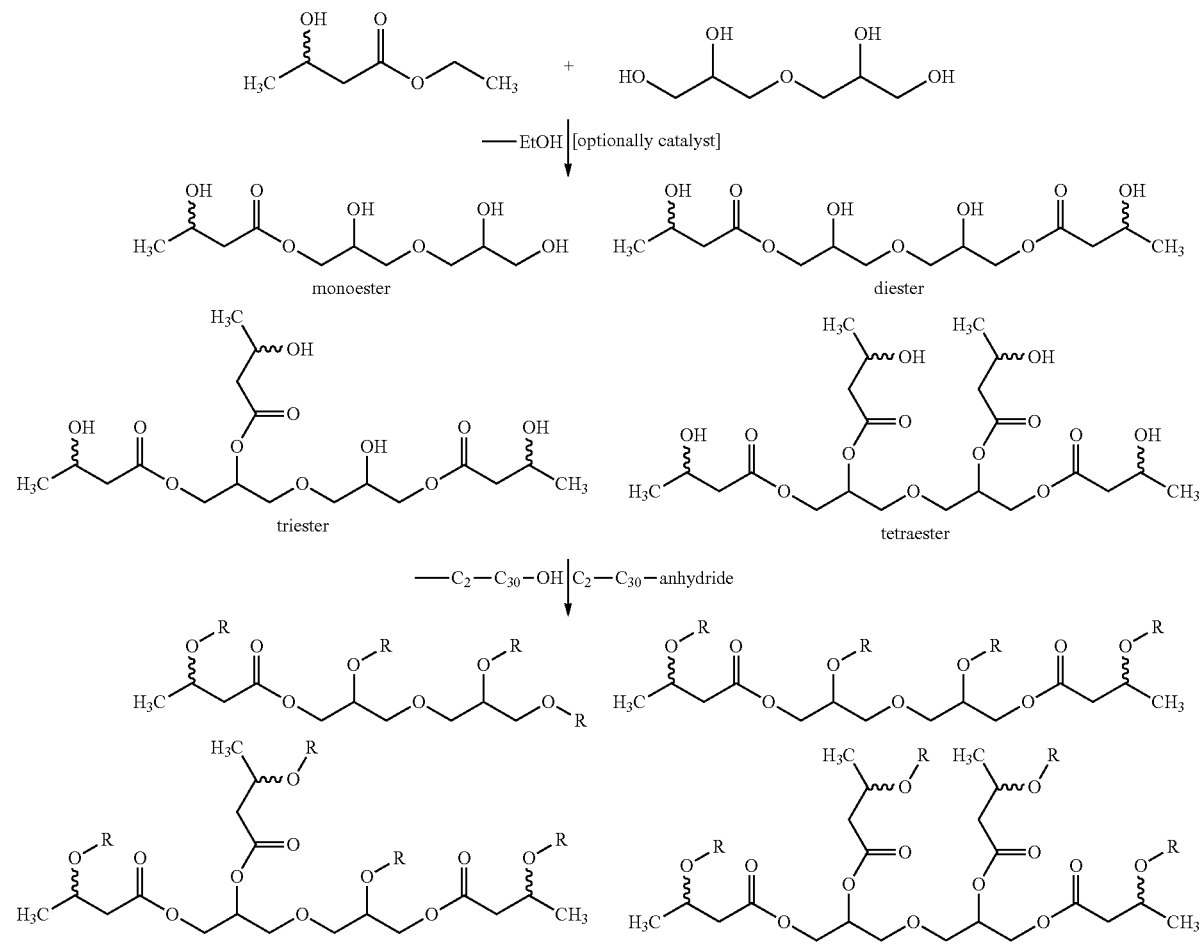

Within the scope of the inventive method, as a reaction product, one or more 3-hydroxybutyric acid polyol esters (III), especially 3-hydroxybutyric acid polyglycerol esters, of the general formula (IIIa)

$$(R^2O)_m\text{—}(X)\text{—}(OR^2)_n \quad (IIIa)$$

may be obtained, wherein, in the general formula (IIIa),

X represents an organic radical, especially a preferentially saturated organic radical comprising 4 to 20 carbon atoms and optionally comprising 1 to 9 oxygen atoms, preferentially selected from an alkyl radical or a (poly) alkyl ether radical, especially a (poly)alkylene glycol radical, more preferably selected from a $C_4$-$C_{20}$-alkyl radical or a $C_4$-$C_{20}$-(poly)alkyl ether radical, especially a $C_4$-$C_{20}$-(poly)alkylene glycol radical, the variables m and n, each independently of one another, represent an integer from 1 to 10, $R^2$, independently of one another, represents: hydrogen, a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, does not represent hydrogen, and with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, the groups $R^2O$— can be in any position of the radical X (preferentially wherein at least one group $R^2O$— is terminal).

Especially, in the above general formula (IIIa), $R^2$, independently of one another, may represent hydrogen or a radical $CH_3$—CH(OH)—$CH_2$—C(O)—, however, with the proviso that at least one radical $R^2$, especially at least two radicals $R^2$, does not represent hydrogen.

Especially, in the above general formula (IIIa), $R^2$, independently of one another, may represent: a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in the above general formula (IIIa), the $C_1$-$C_{29}$-alkyl radical may be a linear (straight chain) or branched, saturated or mono- or polyunsaturated $C_1$-$C_{29}$-alkyl radical; preferably the $C_1$-$C_{29}$-alkyl radical may be a $C_1$-$C_9$-alkyl radical (especially a linear or branched, saturated or mono- or polyunsaturated $C_1$-$C_9$-radical).

Especially, in the production method according to the invention, as a reaction product, one or more 3-hydroxybutyric acid polyol esters (III), especially 3-hydroxybutyric acid polyglycerol esters, of the general formula (IIIb)

$$R^2O\text{—}CH_2\text{—}CH(OR^2)\text{—}CH_2\text{—}[O\text{—}CH_2\text{—}CH(OR^2)\text{—}CH_2]_p\text{—}OR^2 \quad (IIIb)$$

can be obtained, wherein, in the general formula (IIIb), the variable p represents an integer from 1 to 4, especially 1 or 2, preferentially 1, $R^2$, independently of one another, represents: hydrogen, a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, does not represent hydrogen, and with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in the above general formula (IIIb), $R^2$, independently of one another, may represent hydrogen or a radical $CH_3$—CH(OH)—$CH_2$—C(O)—, however, with the proviso that at least one radical $R^2$, especially at least two radicals $R^2$, does not represent hydrogen.

Especially, in the above general formula (IIIb), $R^2$, independently of one another, may represent: a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in the above general formula (IIIb), the $C_1$-$C_{29}$-alkyl radical may be a linear (straight chain) or branched, saturated or mono- or polyunsaturated $C_1$-$C_{29}$-alkyl radical; preferably the $C_1$-$C_{29}$-alkyl radical may be a $C_1$-$C_9$-alkyl radical (especially a linear or branched, saturated or mono- or polyunsaturated $C_1$-$C_9$-radical).

According to a special embodiment of the inventive method, as a reaction product, one or more 3-hydroxybutyric acid polyol esters (III), especially 3-hydroxybutyric acid polyglycerol esters, of the general formula (IIIc)

$$R^2O\text{—}CH_2\text{—}CH(OR^2)\text{—}CH_2\text{—}O\text{—}CH_2\text{—}CH(OR^2)\text{—}CH_2\text{—}OR^2 \quad (IIIc)$$

can be obtained, wherein, in the general formula (IIIc), $R^2$, independently of one another, represents: hydrogen, a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, does not represent hydrogen, and with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in the above general formula (IIIc), $R^2$, independently of one another, may represent hydrogen or a radical $CH_3$—CH(OH)—$CH_2$—C(O)—, however, with the proviso that at least one radical $R^2$, especially at least two radicals $R^2$, does not represent hydrogen.

Especially, in the above general formula (IIIc), $R^2$, independently of one another, may represent: a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in the above general formula (IIIc), the $C_1$-$C_{29}$-alkyl radical may be a linear (straight chain) or branched, saturated or mono- or polyunsaturated $C_1$-$C_{29}$-alkyl radical; preferably the $C_1$-$C_{29}$-alkyl radical may be a $C_1$-$C_9$-alkyl radical (especially a linear or branched, saturated or mono- or polyunsaturated $C_1$-$C_9$-radical).

According to another special embodiment of the inventive method, as a reaction product, a mixture of at least two 3-hydroxybutyric acid polyol esters (III), especially 3-hydroxybutyric acid polyglycerol esters, being different from one another, especially as defined above, can be obtained.

According to another special embodiment of the inventive method, as a reaction product, a mixture of at least three 3-hydroxybutyric acid polyol esters (III), especially 3-hydroxybutyric acid polyglycerol esters, being different from one another, especially as defined above, can be obtained As mentioned hereinbefore, the method according to the invention is usually carried out in the absence of solvents and/or without any solvent (i.e. as a reaction in mass or as a reaction in substance or as a so-called bulk reaction). This has the advantage that the reaction products obtained are not contaminated with solvent and no solvent has to be removed and disposed of or recycled in a costly and energy-intensive manner after the method or reaction has been carried out. Surprisingly, the method or reaction nevertheless proceeds with high conversions and yields and at least essentially without significant by-product formation.

A further subject-matter—according to a second aspect of the present invention—is the reaction product obtainable according to the inventive method or the inventive reaction product as defined hereinabove, respectively, (i.e. one or more 3-hydroxybutyric acid polyol esters, especially 3-hydroxybutyric acid polyglycerol esters, or mixtures thereof).

Especially, the reaction product (i.e. (chemical) product or product mixture) obtainable according to the inventive method or the inventive reaction product as defined hereinabove, respectively, can comprise one or more 3-hydroxybutyric acid polyol esters (III), especially 3-hydroxybutyric acid polyglycerol esters, of the general formula (IIIa)

$$(R^2O)_m\text{—}(X)\text{—}(OR^2)_n \qquad (IIIa)$$

wherein, in the general formula (IIIa),

X represents an organic radical, especially a preferentially saturated organic radical comprising 4 to 20 carbon atoms and optionally comprising 1 to 9 oxygen atoms, preferentially selected from an alkyl radical or a (poly) alkyl ether radical, especially a (poly)alkylene glycol radical, more preferably selected from a $C_4$-$C_{20}$-alkyl radical or a $C_4$-$C_{20}$-(poly)alkyl ether radical, especially a $C_4$-$C_{20}$-(poly)alkylene glycol radical, the variables m and n, each independently of one another, represent an integer from 1 to 10, $R^2$, independently of one another, represents: hydrogen, a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, does not represent hydrogen, and with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—;

especially wherein the groups $R^2O$— are in any position of the radical X, preferentially wherein at least one group $R^2O$— is terminal.

Especially, in this context, in the general formula (IIIa), $R^2$, independently of one another, may represent hydrogen or a radical $CH_3$—CH(OH)—$CH_2$—C(O)—, however, with the proviso that at least one radical $R^2$, especially at least two radicals $R^2$, does not represent hydrogen.

Especially, in the general formula (IIIa), $R^2$, independently of one another, may represent: a radical $CH_3$—CH (OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in the above general formula (IIIa), the $C_1$-$C_{29}$-alkyl radical may be a linear (straight chain) or branched, saturated or mono- or polyunsaturated $C_1$-$C_{29}$-alkyl radical; preferably the $C_1$-$C_{29}$-alkyl radical may be a $C_1$-$C_9$-alkyl radical (especially a linear or branched, saturated or mono- or polyunsaturated $C_1$-$C_9$-radical).

Especially, the reaction product can comprise one or more 3-hydroxybutyric acid polyol esters (III), especially 3-hydroxybutyric acid polyglycerol esters, of the general formula (IIIb)

$$R^2O\text{—}CH_2\text{—}CH(OR^2)\text{—}CH_2\text{—}[O\text{—}CH_2\text{—}CH(OR^2)\text{—}CH_2]_p\text{—}OR^2 \qquad (IIIb)$$

wherein, in the general formula (IIIb), the variable p represents an integer from 1 to 4, especially 1 or 2, preferentially 1, $R^2$, independently of each other, represents: hydrogen, a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, does not represent hydrogen, and with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in this context, in the general formula (IIIb), $R^2$, independently of one another, may represent hydrogen or a radical $CH_3$—CH(OH)—$CH_2$—C(O)—, however, with the proviso that at least one radical $R^2$, especially at least two radicals $R^2$, does not represent hydrogen.

Especially, in the general formula (IIIb), $R^2$, independently of one another, may represent: a radical $CH_3$—CH (OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in the general formula (IIIb), the $C_1$-$C_{29}$-alkyl radical may be a linear (straight chain) or branched, saturated or mono- or polyunsaturated $C_1$-$C_{29}$-alkyl radical; preferably the $C_1$-$C_{29}$-alkyl radical may be a $C_1$-$C_9$-alkyl radical (especially a linear or branched, saturated or mono- or polyunsaturated $C_1$-$C_9$-radical).

According to a particular embodiment of the present invention, the reaction product can especially comprise one or more 3-hydroxybutyric acid polyol esters (III), especially 3-hydroxybutyric acid polyglycerol esters, of the general formula (IIIc)

$$R^2O\text{—}CH_2\text{—}CH(OR^2)\text{—}CH_2\text{—}O\text{—}CH_2\text{—}CH(OR^2)\text{—}CH_2\text{—}OR^2 \qquad (IIIc)$$

wherein, in the general formula (IIIc), $R^2$, independently of one another, represents: hydrogen, a radical $CH_3$—CH (OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, does not represent hydrogen, and with the proviso that at least one radical R², especially at least two radicals R², represents a radical CH₃—CH(OH)—CH₂—C(O)— or a radical CH₃—CH(OR³)—CH₂—C(O)— with R³=(C₁-C₂₉-alkyl)-C(O)—.

Especially, in the general formula (IIIc), R², independently of one another, may represent hydrogen or a radical CH₃—CH(OH)—CH₂—C(O)—, however, with the proviso that at least one radical R², especially at least two radicals R², does not represent hydrogen.

Especially, in the general formula (IIIc), R², independently of one another, may represent: a radical CH₃—CH(OH)—CH₂—C(O)— or a radical CH₃—CH(OR³)—CH₂—C(O)— with R³=(C₁-C₂₉-alkyl)-C(O)— or a radical (C₁-C₂₉-alkyl)-C(O)—, however, with the proviso that at least one radical R², especially at least two radicals R², represents a radical CH₃—CH(OH)—CH₂—C(O)— or a radical CH₃—CH(OR³)—CH₂—C(O)— with R³=(C₁-C₂₉-alkyl)-C(O)—.

Especially, in the general formula (IIIc), the C₁-C₂₉-alkyl radical may be a linear (straight chain) or branched, saturated or mono- or polyunsaturated C₁-C₂₉-alkyl radical; preferably the C₁-C₂₉-alkyl radical may be a C₁-C₉-alkyl radical (especially a linear or branched, saturated or mono- or polyunsaturated C₁-C₉-radical).

According to a specific embodiment, the reaction product may comprise a mixture of at least two 3-hydroxybutyric acid polyol esters (III), especially 3-hydroxybutyric acid polyglycerol esters, being different from one another, especially as defined above.

According to another specific embodiment, the reaction product may comprise a mixture of at least three 3-hydroxybutyric acid polyol esters (III), especially 3-hydroxybutyric acid polyglycerol esters, being different from one another, especially as defined above.

A subject-matter of the present invention is also a 3-hydroxybutyric acid polyol ester, especially 3-hydroxybutyric acid polyglycerol ester, of the general formula (IIIa)

(IIIa)

wherein, in the general formula (IIIa),
X represents an organic radical, especially a preferentially saturated organic radical comprising 4 to 20 carbon atoms and optionally comprising 1 to 9 oxygen atoms, preferentially selected from an alkyl radical or a (poly)alkyl ether radical, especially a (poly)alkylene glycol radical, more preferably selected from a C₄-C₂₀-alkyl radical or a C₄-C₂₀-(poly)alkyl ether radical, especially a C₄-C₂₀-(poly)alkylene glycol radical,
the variables m and n, each independently of one another, represent an integer from 1 to 10,
R², independently of one another, represents: hydrogen, a radical CH₃—CH(OH)—CH₂—C(O)— or a radical CH₃—CH(OR³)—CH₂—C(O)— with R³=(C₁-C₂₉-alkyl)-C(O)— or a radical (C₁-C₂₉-alkyl)-C(O)—, however, with the proviso that at least one radical R², especially at least two radicals R², does not represent hydrogen, and with the proviso that at least one radical R², especially at least two radicals R², represents a radical CH₃—CH(OH)—CH₂—C(O)— or a radical CH₃—CH(OR³)—CH₂—C(O)— with R³=(C₁-C₂₉-alkyl)-C(O)—;
especially wherein the groups R²O— are in any position of the radical X, preferentially wherein at least one group R²O— is terminal.

Especially, in the general formula (IIIa), R², independently of one another, may represent hydrogen or a radical CH₃—CH(OH)—CH₂—C(O)—, however, with the proviso that at least one radical R², especially at least two radicals R², does not represent hydrogen.

Especially, in the general formula (IIIa), R², independently of one another, may represent: a radical CH₃—CH(OH)—CH₂—C(O)— or a radical CH₃—CH(OR³)—CH₂—C(O)— with R³=(C₁-C₂₉-alkyl)-C(O)— or a radical (C₁-C₂₉-alkyl)-C(O)—, however, with the proviso that at least one radical R², especially at least two radicals R², represents a radical CH₃—CH(OH)—CH₂—C(O)— or a radical CH₃—CH(OR³)—CH₂—C(O)— with R³=(C₁-C₂₉-alkyl)-C(O)—.

Especially, in the general formula (IIIa), the C₁-C₂₉-alkyl radical may be a linear (straight chain) or branched, saturated or mono- or polyunsaturated C₁-C₂₉-alkyl radical; preferably the C₁-C₂₉-alkyl radical may be a C₁-C₉-alkyl radical (especially a linear or branched, saturated or mono- or polyunsaturated C₁-C₉-radical).

Another subject-matter of the present invention is also a 3-hydroxybutyric acid polyol ester, especially 3-hydroxybutyric acid polyglycerol ester, especially as defined above,
wherein the 3-hydroxybutyric acid polyol ester corresponds to the general formula (IIIb)

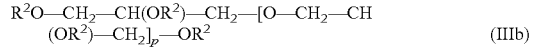

(IIIb)

wherein, in the general formula (IIIb),
the variable p represents an integer from 1 to 4, especially 1 or 2, preferentially 1,
R², independently of one another, represents: hydrogen, a radical CH₃—CH(OH)—CH₂—C(O)— or a radical CH₃—CH(OR³)—CH₂—C(O)— with R³=(C₁-C₂₉-alkyl)-C(O)— or a radical (C₁-C₂₉-alkyl)-C(O)—, however, with the proviso that at least one radical R², especially at least two radicals R², does not represent hydrogen, and with the proviso that at least one radical R², especially at least two radicals R², represents a radical CH₃—CH(OH)—CH₂—C(O)— or a radical CH₃—CH(OR³)—CH₂—C(O)— with R³=(C₁-C₂₉-alkyl)-C(O)—.

Especially, in the general formula (IIIb), R², independently of one another, may represent hydrogen or a radical CH₃—CH(OH)—CH₂—C(O)—, however, with the proviso that at least one radical R², especially at least two radicals R², does not represent hydrogen.

Furthermore, in the general formula (IIIb), R², independently of one another, may represent: a radical CH₃—CH(OH)—CH₂—C(O)— or a radical CH₃—CH(OR³)—CH₂—C(O)— with R³=(C₁-C₂₉-alkyl)-C(O)— or a radical (C₁-C₂₉-alkyl)-C(O)—, however, with the proviso that at least one radical R², especially at least two radicals R², represents a radical CH₃—CH(OH)—CH₂—C(O)— or a radical CH₃—CH(OR³)—CH₂—C(O)— with R³=(C₁-C₂₉-alkyl)-C(O)—.

Especially, in the general formula (IIIb), the C₁-C₂₉-alkyl radical may be a linear (straight chain) or branched, saturated or mono- or polyunsaturated C₁-C₂₉-alkyl radical; preferably the C₁-C₂₉-alkyl radical may be a C₁-C₉-alkyl radical (especially a linear or branched, saturated or mono- or polyunsaturated C₁-C₉-radical).

Again another subject-matter of the present invention is also a 3-hydroxybutyric acid polyol ester, especially 3-hydroxybutyric acid polyglycerol ester, especially as defined above,
wherein the 3-hydroxybutyric acid polyol ester corresponds to general formula (IIIc),

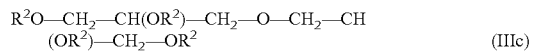

(IIIc)

wherein, in the general formula (IIIc), $R^2$, independently of one another, represents: hydrogen, a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, does not represent hydrogen, and with the proviso that at least one radical $R^2$, especially at least two radicals $R^2$, represents a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)—.

Especially, in the general formula (IIIc), $R^2$, independently of one another, may represent hydrogen or a radical $CH_3$—CH(OH)—$CH_2$—C(O)—, however, with the proviso that at least one radical $R^2$, especially at least two radicals $R^2$, does not represent hydrogen.

Furthermore, in the general formula (IIIc), $R^2$, independently of one another, may represent: a radical $CH_3$—CH(OH)—$CH_2$—C(O)— or a radical $CH_3$—CH($OR^3$)—$CH_2$—C(O)— with $R^3$=($C_1$-$C_{29}$-alkyl)-C(O)— or a radical ($C_1$-$C_{29}$-alkyl)-C(O)—, however, with the proviso that at least one radical $R^2$, especially at least two radicals $R^2$, represents a radical $CH_3$—CH(OH)—$CH_2$—C(O)— or a radical $CH_3$—CH(OR)—$CH_2$—C(O)— with $R^3$=($C_1$-$C_{29}$-alkyl)-C(O)—.

Especially, in the general formula (IIIc), the $C_1$-$C_{29}$-alkyl radical may be a linear (straight chain) or branched, saturated or mono- or polyunsaturated $C_1$-$C_{29}$-alkyl radical; preferably the $C_1$-$C_{29}$-alkyl radical may be a $C_1$-$C_9$-alkyl radical (especially a linear or branched, saturated or mono- or polyunsaturated $C_1$-$C_9$-radical).

A further subject-matter of the present invention according to this aspect of the invention is, according to a special embodiment, a mixture comprising at least two 3-hydroxybutyric acid polyol esters, especially 3-hydroxybutyric acid polyglycerol esters, being different from one another, as defined above.

Again, a further subject-matter of the present invention according to this aspect of the invention is, according to a further special embodiment, a mixture comprising at least three 3-hydroxybutyric acid polyol esters, especially 3-hydroxybutyric acid polyglycerol esters, being different from one another, as defined above.

The reaction product obtainable according to the inventive method or the inventive reaction product as defined hereinabove, respectively, and/or the 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or the mixture, obtainable according to the inventive production method or the inventive mixture as defined hereinabove, respectively, comprises a multitude of advantages and special features compared to the prior art:

As the applicant has surprisingly found out, the reaction product obtainable according to the inventive method or the inventive reaction product as defined hereinabove, respectively, and/or the 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or the mixture, obtainable according to the inventive production method or the inventive mixture as defined hereinabove, respectively, is suitable as a precursor or metabolite of 3-hydroxybutyric acid or its salts, since, on the one hand, it is converted physiologically, especially in the gastrointestinal tract, to 3-hydroxybutyric acid or its salts and, on the other hand, it simultaneously comprises a good physiological compatibility or tolerability, especially with regard to non-toxicity and acceptable organoleptic properties.

Moreover, the reaction product obtainable according to the inventive method or the inventive reaction product as defined hereinabove, respectively, and/or the 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or the mixture, obtainable according to the inventive production method or the inventive mixture as defined hereinabove, respectively, is easily accessible or available on a large scale on a synthetic basis, even on a commercial scale, and with the required pharmaceutical or pharmacological quality.

Additionally, the reaction product obtainable according to the inventive method or the inventive reaction product as defined hereinabove, respectively, and/or the 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or the mixture, obtainable according to the inventive production method or the inventive mixture as defined hereinabove, respectively, can, if necessary, be provided in enantiomerically pure or enantiomerically enriched form.

The reaction product obtainable according to the inventive method or the inventive reaction product as defined hereinabove, respectively, and/or the 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or the mixture, obtainable according to the inventive production method or the inventive mixture as defined hereinabove, respectively, thus represents an efficient pharmacological drug target in the context of keto-body therapy of the human or animal body.

In the following, the remaining aspects of the invention are explained in more detail.

A further subject-matter of the present invention—according to a third aspect of the present invention—is a pharmaceutical composition, especially a drug or medicament, which comprises a reaction product obtainable according to the inventive production method or the inventive reaction product as defined hereinabove, respectively, and/or a 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or a mixture, obtainable according to the inventive production method or the inventive mixture as defined hereinabove, respectively.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Again, a further subject-matter of the present invention—according to a fourth aspect of the present invention—is a reaction product obtainable according to the inventive production method or the inventive reaction product as defined hereinabove, respectively, and/or a 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or a mixture, obtainable according to the inventive production method or the inventive mixture as defined hereinabove, respectively, for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a fifth aspect of the present invention—is the use of a reaction product obtainable according to the inventive production method or the inventive reaction product as defined hereinabove, respectively, and/or a 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or a mixture, obtainable according to the inventive production method or the inventive mixture as defined hereinabove, respectively, for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a sixth aspect of the present invention—is the use of a reaction product obtainable according to the inventive production method or the inventive reaction product as defined hereinabove, respectively, and/or a 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or a mixture, obtainable according to the inventive production method or the inventive mixture as defined hereinabove, respectively, for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to a seventh aspect of the present invention—is a food and/or a food product, which comprises a reaction product obtainable according to the inventive production method or the inventive reaction product as defined hereinabove, respectively, and/or a 3-hydroxybutyric acid polyol ester, especially 3-hydroxybutyric acid polyglycerol ester, obtainable according to the inventive production method or the inventive 3-hydroxybutyric acid polyol ester, especially 3-hydroxybutyric acid polyglycerol ester, as defined hereinabove, respectively, and/or a mixture, obtainable according to the inventive production method or the inventive mixture as defined hereinabove, respectively.

According to a particular embodiment, the food and/or the food product may essentially be a dietary supplement, a functional food, a novel food, a food additive, a food supplement, a dietary food, a power snack, an appetite suppressant or a strength and/or endurance sport supplement.

Finally, yet another subject-matter of the present invention—according to an eighth aspect of the present invention—is the use of a reaction product, as defined hereinabove, obtainable according to the inventive production method and/or a mixture, as defined hereinabove, obtainable according to the inventive production method in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and non-limiting implementation and configuration of the present invention.

EXAMPLES

Abbreviations Used

3-BHB-ethyl=3-hydroxybutyric acid ethyl ester (starting compound)
3-BHB-FS=3-hydroxybutyric acid (reaction by-product)
PG(2)=diglycerol: HO—$CH_2$—CH(OH)—$CH_2$—O—$CH_2$—CH(OH)—$CH_2$—OH
n.d.=not determined
3-BHB dimer=reaction by-product of the following formula:

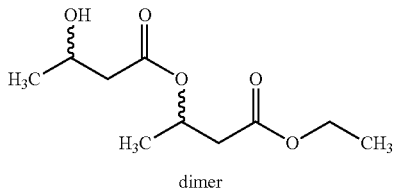

dimer

Examples of Production

The inventive production method is illustrated by the following examples. The relevant general reaction scheme is shown and explained in the general description section.

Production of 3-BHB-diglycerol Ester Mixtures

In a 4,000-ml-multi-neck flask with dephlegmator (partial condenser) and distillation bridge, 3,000 g (R)/(S)-3-hydroxybutyric acid ethyl ester (racemic), 450 g digylcerol and 14 g immobilized enzyme (CALB lipase on polymer support, derived from *Candida antarctica*, e. g. Novozym® 435 from Sigma-Aldrich or Merck or Lipozym® 435 from Strem Chemicals, Inc.) are provided.

The reaction mixture is stirred at 70° C. and under vacuum (<500 mbar) for 50 h. The enzyme is then filtered out and the excess 3-hydroxybutyric acid ethyl ester is distilled off under vacuum. The residue obtained is steam-treated in a high vacuum for 2 to 4 hours (steam temperature: 160° C.).

According to analytical examination, the residue consists of 17% 3-BHB-mono-diglycerol ester, 46% 3-BHB-di-diglycerol ester, 22% 3-BHB-tri-diglycerol ester, 2% 3-BHB-tetra-diglycerol ester, 2% 3-hydroxybutyric acid, 7% 3-hydroxybutyric acid dimer and 2% diglycerol. The characterization is performed by means of GC, GPC and GC-MS.

In the course of purification, educts and reaction by-products are removed so that a pure mixture is obtained. Part of the mixture is separated by chromatography to obtain the different diglycerol esters as pure substances (i.e. pure 3-BHB-mono-diglycerol ester, pure 3-BHB-di-diglycerol ester, pure 3-BHB-tri-diglycerol ester and pure 3-BHB-tetra-diglycerol ester). Another part of the mixture is subjected to separation by fractional distillation.

Further Production of 3-BHB-diglycerol Ester Mixtures

The previous test is repeated, but with sodium methylate (NaOMe) as catalyst (1% by weight) instead of the enzyme and at temperatures between 100 and 120° C. (40 mol-% excess of 3-BHB ethyl ester). Comparable results are obtained. Purification and separation or fractionation are performed in the same way.

Further Production of 3-BHB-diglycerol Ester Mixtures

The previous experiment with sodium methylate (NaOMe) as catalyst is repeated, but with other polyols (namely with polyglycerol PG(3) and with 1,2-pentanediol). Comparable results are obtained. Purification and separation or fractionation are performed in the same way.

Further Production Examples

Various polyol components based on polyhydric alcohols are enzymatically reacted with 3-BHB-ethyl ester.

The polyalcohols selected are 1,2-pentanediol and diglycerol PG(2). The respective alcohols are reacted at 70° C. for 24 h with immobilized enzyme (CALB lipase on polymer support, derived from *Candida antarctica*, e.g. Novozym® 435 from Sigma-Aldrich or Merck or Lipozym® 435 from Strem Chemicals, Inc.) (in each case 1% by weight enzyme and 40 mol-% excess 3-BHB-ethyl ester).

The aforementioned polyalcohols 1,2-pentanediol and diglycerol PG(2) are efficiently converted to the desired products by the aforementioned enzymes. Comparable results to the previous experiments are obtained. Purification and separation or fractionation are performed in the same way.

The experiments are repeated with sodium methylate (NaOMe) as catalyst instead of the enzymes and at temperatures between 100 and 120° C. Comparable results are obtained. Purification and separation or fractionation are performed in the same way.

Since especially the 3-BHB-PG(2) esters only have a slightly bitter taste, in particular these esters are an efficient product group for therapeutic applications. Therefore, the preceding experiment with enzyme and diglycerol PG(2) as polyalcohol is performed on a larger scale (2 to 4 kg).

First, the stoichiometric reaction conditions of the previous experiments are applied on a scale of 2 kg (40 mol-% excess 3-BHB ethyl ester, 1% by weight enzyme). After 15 h, a portion of the reaction mixture (approx. 200 g) is removed for further testing. This is a mono/di-PG(2) ester mixture. Afterwards, another approx. 2 kg of 3-BHB-ethyl ester are added. The amount corresponds to an excess of 100 mol-%, already calculated on the (R)-enantiomer. The aim is to produce a full ester. It can be seen that after about 20 to 30 h a constant content of di-PG(2) ester is obtained; the mono-PG(2) ester portion decreases and the tri-PG(2) ester portion increases. Further analyses (GPC) show that a tetra-PG(2) ester has also formed.

After distilling off excess 3-BHB-ethyl ester, the initially obtained (low-boiling) mono/di-PG(2)-ester mixture has only a slightly bitter taste, while the higher (higher-boiling) di-/tri/tetra-PG(2)-ester mixture has a slightly stronger bitter taste. However, both mixtures are organoleptically acceptable and compatible. Furthermore, they are still raw esters, which still contain e.g. 3-BHB-dimer, which as a pure substance also has a bitter taste.

After further purification with removal of residual starting compounds and reaction byproducts, a pure mixture with significantly improved organoleptic properties is obtained.

Again Further Production Examples

Production of 3-BHB-diglycerol Ester Mixtures of Diglycerol and 3-hydroxybutyric Acid Ethyl Ester by Basic Catalysis In a 1,000 ml-multi-neck flask with dephlegmator (partial condenser) and distillation bridge, 350 g (R)/(S)-3-hydroxybutyric acid ethyl ester (racemic) and 110 g diglycerol are provided at 80° C. under $N_2$ atmosphere. 15 g of a 30% by weight sodium methanolate solution (NaOMe solution) in methanol at 100° C. are added dropwise to the reaction mixture. The vacuum is then gradually reduced to <100 mbar and the reaction mixture is stirred for another 12 h. The excess 3-BHB-ethyl ester is then distilled off under reduced vacuum (<20 mbar). The reaction product is a 3-BHB-diglycerol ester mixture.

Production of 3-BHB-diglycerol Ester Mixtures of Diglycerol and 3-hydroxybutyric Acid Ethyl Ester by Enzymatic Catalysis 3,000 g (R)/(S)-3-hydroxybutyric acid ethyl ester (racemic), 450 g diglycerol and 14 g immobilized enzyme (CALB) are provided in a 4,000 ml multi-neck flask with dephlegmator (partial condenser) and distillation bridge. The reaction mixture is stirred at 70° C. and under vacuum (<500 mbar) for 50 h. The enzyme is then filtered out and the excess 3-hydroxybutyric acid ethyl ester is distilled off under vacuum. The residue obtained is steamed for 2 to 4 h in high vacuum (steam temperature: 160° C.). After analytical examination the residue consists of 17% mono-diglycerol ester, 46% di-diglycerol ester, 22% tri-diglycerol ester, 2% tetra-diglycerol ester, 2% 3-hydroxybutyric acid, 7% 3-hydroxybutyric acid dimer and 2% diglycerol. The characterization is performed by GC, GPC and GC-MS.

Functionalization Tests

The higher (high-boiling) di-/tri-PG(2) ester mixture obtained in the previous experiment is subsequently functionalized by reaction with $C_7$-anhydride to obtain products fully esterified at all OH-groups. The corresponding general reaction scheme is shown and explained in the general description section.

The experiments show that the intended functionalization by reaction with $C_7$-anhydride leads to the desired products (i.e. esterification of the free OH-groups), as confirmed by appropriate analysis.

Comparable functionalization experiments are also carried out with higher carboxylic acid anhydrides (each with $C_{10}$-, $C_{20}$- and $C_{28}$-carboxylic acid anhydrides) and lead to analogous results (i.e. esterification of the free OH-groups), as confirmed by appropriate analysis.

Physiological Application Tests: In-Vitro Digestion Tests

Digestion Experiments (Splitting or Cleavage Experiments) of Inventive

3-BHB-PG(2)-ester Mixtures

By means of cleavage experiments it is shown that 3-BHB-PG(2) esters or their mixtures, including reaction by-products such as dimers etc., produced according to the invention, can be cleaved in the human gastrointestinal tract.

A purified mixture of 3-BHB-mono-diglycerol ester, 3-BHB-di-diglycerol ester, 3-BHB-tri-diglycerol ester and 3-BHB-tetra-diglycerol ester obtained by the method according to the invention is used as the starting mixture on the one hand and a purified mixture of 3-BHB-mono-diglycerol ester and 3-BHB-di-diglycerol ester obtained by the process according to the invention on the other hand.

For the cleavage experiments under near-body conditions two media are investigated:
FaSSGF, which simulates the stomach
FaSSIF, which simulates the intestinal tract
Both media are from the company Biorelevant®, Ltd. in Great Britain. In addition, in some experiments porcine pancreas is added (Panzytrat® 40,000, Fa. Allergan).

The results of the cleavage experiments in a FaSSGF or FaSSIF medium with Panzytrat® and without Panzytrat® (both 35° C., 24 h) show that the samples hydrolyze under FaSSGF conditions with Panzytrat® and without Panzytrat®; this is mainly due to the low pH value (pH=1.6) of the medium. Under FaSSIF conditions, a lower conversion using Panzytrat® takes place.

In all experiments it can be seen that the cascade (tetraester becomes triester, triester becomes diester etc.) continues until the desired free acid 3-BHB or 3-BHB-FS is obtained.

Further Digestion Experiments (Cleavage Experiments) of Inventive

3-BHB-PG(2)-ester Mixtures

Cleavage Experiments with Pancreatin 2 g of a mixture prepared as described above based on 3-BHB-mono-diglycerol ester, 3-BHB-di-diglycerol ester, 3-BHB-tri-diglycerol ester and 3-BHB-tetra-diglycerol ester is dissolved in 50 g water and 0.5 g (1% by weight) pancreatin is added. The pancreatin is used in the form of the commercially available product Panzytrat® 40,000 from the Allergan company. The whole mixture is stirred on a hot plate at 50° C.; the course of the reaction is determined and monitored by continuously recording the acid number over time. The acid number increases over the observation period (cleavage of the 3-BHB-diglycerol ester mixture to the free acid). The conversion/time course of the aqueous cleavage of the mixture of esters according to the invention by means of pancreatin, including the increase in the acid number over time, demonstrates the desired decomposition of the educt mixture to the free acid. This is confirmed by appropriate analysis. The experiment proves that the starting mixture (educt mixture) according to the invention is a suitable physiological precursor for 3-hydroxybutyric acid for the corresponding keto-body therapies.

The test is repeated and verified on the basis of the individual esters in pure form. Comparable results are obtained, i.e. both the 3-BHB-mono-diglycerol ester and the 3-BHB-di-diglycerol ester as well as the 3-BHB-tri-diglycerol ester and the 3-BHB-tetra-diglycerol ester are cleaved by pancreatin to the free 3-hydroxybutyric acid.

The previously described cleavage experiments prove that the polyol esters, especially polyglycerol esters, of 3-hydroxybutyric acid are efficient precursors or metabolites of free hydroxybutyric acid or its salts, especially with regard to their intended effect, which are present in physiologically compatible or physiologically compatible form.

The invention claimed is:

1. A method for producing polyglycerol esters of 3-hydroxybutyric acid, the method comprising:
reacting at least one compound of the general formula (I)

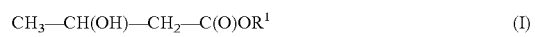

wherein, in the general formula (I), the radical $R^1$ represents hydrogen or $C_1$-$C_4$-alkyl,
with at least one polyglycerol of the general formula (IIb)

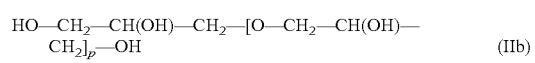

wherein, in the general formula (IIb), the variable p represents an integer from 1 to 4,
to obtain one or more 3-hydroxybutyric acid polyglycerol esters,
and a compound of the general formula (IV)

wherein, in the general formula (IV), the radical $R^1$ represents hydrogen or $C_1$-$C_4$-alkyl, wherein the reaction is carried out in the absence of any solvents, wherein the reaction is carried out in the presence of a catalyst, and wherein the method further comprises continuously withdrawing the compound according to the general formula (IV) from the reaction.

2. The method according to claim 1, wherein, the compound of the general formula (I) is 3-hydroxybutyric acid ethyl ester of the formula $CH_3$—$CH(OH)$—$CH_2$—$C(O)OC_2H_5$.

3. The method according to claim 1, wherein the catalyst is selected from among enzymes and metal-containing catalysts; and wherein the catalyst is recycled after the reaction.

4. The method according to claim 1, wherein the compound of the general formula (I) and the polyglycerol (IIb) are used in a molar ratio of compound of the general formula (I)/polyglycerol (IIb) in a range of from 1:1 to 10:1.

5. The method according to claim 1, wherein the polyglycerol (IIb) is a diglycerol of formula (IIc)

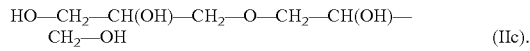

6. The method according to claim 1, wherein the reaction product obtained is fractionated after the reaction has been performed.

7. The method according to claim 1, wherein unreacted starting compounds selected from among starting compounds (I) and (IIb) are separated from the reaction product and are subsequently recycled.

8. The method according to claim 1, wherein the reaction is followed by an at least partial esterification of hydroxyl groups which are still present, wherein the esterification is carried out by reaction with a $C_2$-$C_{30}$-carboxylic acid anhydride.

9. A polyglycerol ester of 3-hydroxybutyric acid obtainable by the method according to claim 1.

10. A polyglycerol ester of 3-hydroxybutyric acid, wherein the polyglycerol ester of 3-hydroxybutyric acid corresponds to the general formula (IIIb)

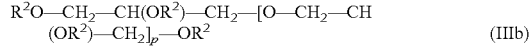

wherein, in the general formula (IIIb),
the variable p represents an integer from 1 to 4,
$R^2$, independently of one another, represents: hydrogen, a radical $CH_3$—$CH(OH)$—$CH_2$—$C(O)$— a radical $CH_3$—$CH(OR^3)$—$CH_2$—$C(O)$— or a radical $R^3$, however, with the proviso that at least one radical $R^2$ does not represent hydrogen, and with the proviso that at least one radical $R^2$ represents a radical $CH_3$—$CH(OH)$—$CH_2$—$C(O)$— or a radical $CH_3$—$CH(OR^3)$—$CH_2$—$C(O)$—, and
$R^3$ represents the radical $(C_1$-$C_{29}$-alkyl)-$C(O)$—.

11. The polyglycerol ester of 3-hydroxybutyric acid according to claim 10 wherein, in the general formula (IIIb), $R^2$, independently of one another, represents hydrogen or a radical $CH_3$—$CH(OH)$—$CH_2$—$C(O)$—, however, with the proviso that at least one radical $R^2$ does not represent hydrogen.

12. The polyglycerol ester of 3-hydroxybutyric acid according to claim 10, wherein, in the general formula (IIIb), $R^2$, independently of one another, represents: a radical $CH_3$—$CH(OH)$—$CH_2$—$C(O)$— a radical $CH_3$—$CH(OR^3)$—$CH_2$—$C(O)$— or a radical $R^3$, however, with the proviso that at least one radical $R^2$ represents a radical $CH_3$—$CH(OH)$—$CH_2$—$C(O)$— or a radical $CH_3$—$CH(OR^3)$—$CH_2$—$C(O)$—, and wherein, $R^3$ represents the radical $(C_1$-$C_{29}$-alkyl)-$C(O)$—.

13. The polyglycerol ester of 3-hydroxybutyric acid according to claim 10, wherein the polyglycerol ester of 3-hydroxybutyric acid corresponds to general formula (IIIc),

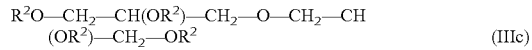

wherein, in the general formula (IIIc), $R^2$, independently of one another, represents: hydrogen, a radical $CH_3$—$CH(OH)$—$CH_2$—$C(O)$— a radical $CH_3$—$CH(OR^3)$—$CH_2$—$C(O)$— or a radical $R^3$, however, with the proviso that at least one radical $R^2$ does not represent hydrogen, and with the proviso that at least one radical $R^2$ represents a radical $CH_3$—$CH(OH)$—$CH_2$—$C(O)$— or a radical $CH_3$—$CH(OR^3)$—$CH_2$—$C(O)$—, and wherein $R^3$ represents the radical $(C_1$-$C_{29}$-alkyl)-$C(O)$—.

14. The polyglycerol ester of 3-hydroxybutyric acid according to claim 13, wherein, in the general formula (IIIc), $R^2$, independently of one another, represents hydrogen or a radical $CH_3$—$CH(OH)$—$CH_2$—$C(O)$—, however, with the proviso that at least one radical $R^2$ does not represent hydrogen.

15. The polyglycerol ester of 3-hydroxybutyric acid according to claim 13, wherein, in the general formula (IIIc), $R^2$, independently of one another, represents: a radical $CH_3$—$CH(OH)$—$CH_2$—$C(O)$— a radical $CH_3$—$CH(OR^3)$—$CH_2$—$C(O)$— or a radical $R^3$, however, with the proviso that at least one radical $R^2$ represents a radical $CH_3$—$CH(OH)$—$CH_2$—$C(O)$— or a radical $CH_3$—$CH(OR^3)$—$CH_2$—$C(O)$—, and wherein $R^3$ represents the radical $(C_1$-$C_{29}$-alkyl)-$C(O)$—.

16. A mixture comprising at least two different polyglycerol esters of 3-hydroxybutyric acid as defined in claim 10.

17. A pharmaceutical composition, wherein the pharmaceutical composition comprises at least one polyglycerol ester of 3-hydroxybutyric acid, wherein the polyglycerol ester of 3-hydroxybutyric acid corresponds to the general formula (IIIb)

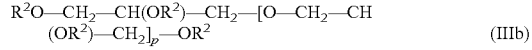

wherein, in the general formula (IIIb),
the variable p represents an integer from 1 to 4,
$R^2$, independently of one another, represents: hydrogen, a radical $CH_3$—$CH(OH)$—$CH_2$—$C(O)$— a radical $CH_3$—$CH(OR^3)$—$CH_2$—$C(O)$— or a radical $R^3$, however, with the proviso that at least one radical $R^2$ does not represent hydrogen, and with the proviso that at least one radical $R^2$ represents a radical $CH_3$—$CH(OH)$—$CH_2$—$C(O)$— or a radical $CH_3$—$CH(OR^3)$—$CH_2$—$C(O)$—, and
$R^3$ represents the radical $(C_1$-$C_{29}$-alkyl)-$C(O)$—.

18. The pharmaceutical composition according to claim 17, wherein the pharmaceutical composition is a drug or a medicament.

19. A method of treating a human suffering from a disease associated with a disorder of the keto-body metabolism, the method comprising a step of administering to said human a pharmaceutical composition comprising at least one polyglycerol ester of 3-hydroxybutyric acid, wherein the polyglycerol ester of 3-hydroxybutyric acid corresponds to the general formula (IIIb)

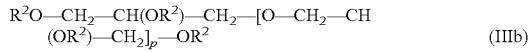   (IIIb)

wherein, in the general formula (IIIb),
the variable p represents an integer from 1 to 4,
$R^2$, independently of one another, represents: hydrogen, a radical $CH_3$—CH(OH)—$CH_2$—C(O)— a radical $CH_3$—CH($OR^3$)—$CH_2$—C(O)— or a radical $R^3$, however, with the proviso that at least one radical $R^2$ does not represent hydrogen, and with the proviso that at least one radical $R^2$ represents a radical $CH_3$—CH(OH)—$CH_2$—C(O)— or a radical $CH_3$—CH($OR^3$)—$CH_2$—C(O)—, and
$R^3$ represents the radical ($C_1$-$C_{29}$-alkyl)-C(O)—.

20. The method according to claim 19,
wherein the disease associated with a keto-body metabolism is selected from the group consisting of craniocerebral trauma, stroke, hypoxia, cardiovascular diseases, myocardial infarction, refeeding syndrome, anorexia, epilepsy, neurodegenerative diseases, dementia, Alzheimer's disease, Parkinson's disease, multiple sclerosis, amyotrophic lateral sclerosis, fat metabolic diseases, glucose transporter defect (GLUT1 defect), VL-FAOD, mitochondriopathies, mitochondrial thiolase defect, Huntington's disease, cancers, T-cell lymphomas, astrocytomas, glioblastomas, HIV, rheumatic diseases, rheumatoid arthritis, arthritis urica, diseases of the gastrointestinal tract, chronic inflammatory bowel diseases, ulcerative colitis, Crohn's disease, lyosomal storage diseases, sphingolipidosis, Niemann-Pick disease, diabetes mellitus and effects of chemotherapy.

21. A food product,
wherein the food product comprises at least one polyglycerol ester of 3-hydroxybutyric acid,
wherein the polyglycerol ester of 3-hydroxybutyric acid corresponds to the general formula (IIIb)

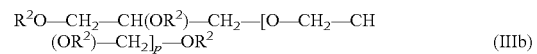   (IIIb)

wherein, in the general formula (IIIb),
the variable p represents an integer from 1 to 4,
$R^2$, independently of one another, represents: hydrogen, a radical $CH_3$—CH(OH)—$CH_2$—C(O)— a radical $CH_3$—CH($OR^3$)—$CH_2$—C(O)— or a radical $R^3$, however, with the proviso that at least one radical $R^2$ does not represent hydrogen, and with the proviso that at least one radical $R^2$ represents a radical $CH_3$—CH(OH)—$CH_2$—C(O)— or a radical $CH_3$—CH($OR^3$)—$CH_2$—C(O)—, and
$R^3$ represents the radical ($C_1$-$C_{29}$-alkyl)-C(O)—.

* * * * *